(12) United States Patent
Brunner et al.

(10) Patent No.: US 9,004,917 B2
(45) Date of Patent: Apr. 14, 2015

(54) DEVICE FOR DETECTING MOVEMENTS OF A LOWER JAW

(75) Inventors: Wolfgang Brunner, Isny im Allgäu (DE); Bernd Kordass, Greifswald (DE)

(73) Assignee: Zebris Medical GmbH, Isny Im Allgau (DE)

( * ) Notice: Subject to any disclaimer, the term of this patent is extended or adjusted under 35 U.S.C. 154(b) by 63 days.

(21) Appl. No.: 13/813,959

(22) PCT Filed: Jul. 20, 2011

(86) PCT No.: PCT/EP2011/062417
§ 371 (c)(1),
(2), (4) Date: Mar. 3, 2013

(87) PCT Pub. No.: WO2012/016832
PCT Pub. Date: Feb. 9, 2012

(65) Prior Publication Data
US 2013/0157218 A1 Jun. 20, 2013

(30) Foreign Application Priority Data
Aug. 2, 2010 (DE) .......................... 10 2010 033 109

(51) Int. Cl.
*A61C 19/045* (2006.01)
(52) U.S. Cl.
CPC .................... *A61C 19/045* (2013.01)

(58) Field of Classification Search
USPC ........... 433/27, 29, 37, 45, 46, 68, 69, 73, 75, 433/140; 600/590; 382/128
See application file for complete search history.

(56) References Cited

U.S. PATENT DOCUMENTS

| | | | | |
|---|---|---|---|---|
| 3,987,548 A | * | 10/1976 | Jones | 433/45 |
| 4,303,077 A | * | 12/1981 | Lewin et al. | 600/590 |
| 4,673,352 A | * | 6/1987 | Hansen | 433/69 |
| 4,836,778 A | * | 6/1989 | Baumrind et al. | 433/69 |
| 4,859,181 A | * | 8/1989 | Neumeyer | 433/69 |
| 5,143,086 A | * | 9/1992 | Duret et al. | 600/590 |
| 6,621,491 B1 | * | 9/2003 | Baumrind et al. | 345/419 |

* cited by examiner

*Primary Examiner* — Ralph Lewis
(74) *Attorney, Agent, or Firm* — Mark M. Friedman

(57) ABSTRACT

Apparatus for detecting motions of a lower jaw relative to the upper jaw of a vertebrate, comprising a first holder (30) to be fixed to the head of a vertebrate with a fixed assignment relative to the upper jaw for accommodating transmitter or receiver units of a position determining system (1) for the detection of motion, a second holder (40A) to be fixed to the lower jaw on the left side for accommodating corresponding left-sided receiver and transmitter units of the position determining system, a third holder (40B) to be fixed to the lower jaw on the right side for accommodating corresponding right-sided receiver and transmitter units of the position determining system, and a first evaluation unit (13) for processing signals from the receiver units so as to generate a differentiated dynamic image of the motions of the left and right sides of the lower jaw from relative positional changes of the transmitter units (11) which are associated with the motions of the lower jaw and are detected by the receiver units.

17 Claims, 2 Drawing Sheets

DEVICE FOR DETECTING MOVEMENTS OF A LOWER JAW

TECHNICAL FIELD AND BACKGROUND

The invention relates to an apparatus for detecting motions of a lower jaw relative to the upper jaw of a vertebrate.

An apparatus and a method for determining all degrees of the freedom of motion and positions of the lower jaw relative to the upper jaw are described, for instance, in DE 10 2004 002 953 A1, which are based on the time delay measurement of ultrasonic pulses between transmitters and receivers of an ultrasonic system, with the aim to improve the measuring accuracy at significant virtual points, especially in the area of the jaw joint, with respect to the measured paths of motion and positions in space.

DE 35 00 305 A1 describes an apparatus for measuring the positions and motions of the lower jaw relative to the upper jaw. A first holder is fixed stationarily to the head of patient, and a second holder is provided at the lower jaw. The first holder comprises a plurality of receivers for ultrasonic pulses, and the second holder includes a plurality of ultrasonic transmitters which are arranged in a distributed manner. A transmitted ultrasonic pulse is successively received by the receivers of the first holder. The delay times of the transmitted ultrasonic pulses give information on the distances of an ultrasonic receiver from an ultrasonic transmitter, thereby allowing the exact detection and analysis of the motions of the lower jaw relative to the upper jaw. At the same time, all degrees of freedom of the system are uniquely detected.

These measuring systems are significant above all in the field of dentistry. For the production of dental prosthesis the teeth of the upper and lower jaws are used as models in articulators (mechanical motion simulators). This allows the reproduction of the motions of the patient's jaws and teeth, and prosthetic measures can be verified and optimized. These motions differ individually in every human being and depend significantly on the anatomy of the jaw joint. The exact detection of the individual motion sequences of the jaw joint, for instance, during chewing motions is important in order to minimize or avoid complex and cost-intensive follow-up treatments after the dental prosthesis or implant were implanted in the patient.

Document DE 10 2004 002 953 A1 of the applicant provides for an improved measuring system of this type, which allows in particular to obtain more exact measuring results.

So far, the detection and simulation of motion was based primarily on mechanistic model concepts as far as the motion sequences of the jaws relative to one another are concerned, especially since a mechanical articulator is by any account rigid and torsionally stiff in terms of construction and only contains rigid jaw models (usually made of plaster). Only the modern possibilities, which allow the scanning of jaws as a whole or of jaw sections, permit the consideration of biological and neurophysiological aspects in the simulation of motions.

It is known that the lower jaw brace bends when muscular strength is applied. If the mouth is widely opened—without much muscular strength—the lower jaw brace already bends inwardly in the area of the wisdom tooth, for instance by about 0.5 mm. These effects are even stronger in closing motions, namely always when occlusal forces are involved, e.g. during chewing or grinding/pressing of the teeth.

As one of the most crucial purposes of the chewing system is the comminution of food it is at any rate sensible and important to identify the effects of chewing forces on the bending of the lower jaw brace during the chewing, as this is the only way to construct chewing surfaces optimally with regard to the dynamic conditions in the chewing system in prosthetic-restorative measures. However, also the grinding and pressing of teeth—a frequent habit for stress reduction—may involve enormous forces which act uncontrollably for a longer period on teeth, jaws and joints, mainly at night, and result in abnormal functional and structural changes of the chewing system, especially in craniomandibular dysfunctions (CMD syndrome).

Therefore, it is the dentist's job to construct or arrange chewing surfaces or artificial teeth such that they are not only suited for the comminution of food, but also for the "reduction of stress", i.e. that they are able to carry loads as optimally as possible or absorb and divert forces, thus protecting the jaw joints. Usually, this protective effect is obtained by specific occlusion concepts, e.g. the construction of a sequential tooth occlusion, where in lateral motions tooth surfaces are successively or sequentially loaded from the canine teeth to the side teeth. The dental technician tendentially makes the angle steeper than necessary in order to have "security reserves" which might be needed for bending the lower jaw, but which are unknown in the individual patient case. To provide a remedy in order to allow the construction of individual chewing surfaces is an important goal.

However, there is also a characteristic difference between the two jaw halves of the lower jaw during the chewing. Depending on the side where the chewing material is interposed between the rows of teeth a working side (=chewing material) and a balance side are formed. The working side is the side where the chewing material is located. During the chewing the lower jaw is initially opened slightly toward the opposite side and then pivots slightly to the working side until the maximum opening position is reached. In the closing motion the teeth grasp the chewing material initially with their cusp tips in a sideways pivoted cusp-to-cusp position and then comminute/squeeze the chewing material by the rows of teeth approaching one another when chewing force is applied. The rows of teeth slide along the cusp facets and cusp slopes into the scissor bite position of the initial toothing. The chewing material is successively comminuted in rhythmic cycles until it can be swallowed. The chewing muscles are equally active on both sides during the chewing motion, i.e. on the working side and the balance side, and bend the lower jaw brace during the comminution. The working side and the balance side virtually decouple themselves in the approaching motion of the chewing surfaces and would actually have to be recorded separately. For this is the only way how steepnesses of the cusp facets can be optimally constructed for the balancing motions and the working motions.

These dynamic aspects of the effect of biting forces can, so far, not be incorporated by the usual measuring systems. Merely the muscle activity as such is easy to detect by means of electromyographical measurements with surface electrodes which are placed on the skin above the muscle bellies. However, there are no measured values that allow the sensible detection and quantification of the individual deflections and deformations of the working side on the one hand and the balance side on the other hand. If mechanical motion simulators are used such additional information can hardly be considered. They demonstrate at best where the mechanical model is inadequate and to what extent and where dental restorations such as crowns, bridges and prostheses in the mouth cavity have to be corrected and adapted. As the future belongs to the so-called virtual articulators, however, which make the scanned rows of teeth visible on the computer screen and available in the computer, dynamic conditions and effects can be reasonably represented and implemented for the first time.

The dynamic behavior of the lower jaw brace, specifically the deformation resultant from force fit and occlusal force, plays a central role for the diagnosis and treatment planning relating to bony structures, e.g. the planing of implants, including the prostheses and crowns that have to be carried and supported by the implants. Implants are "osseointegrated" as artificial roots, in marked contrast to the parodontal, i.e. fibrous anchorage of natural teeth in the tooth bed. For this reason, implants have no or only a very small functional intrinsic mobility and, therefore, transfer occlusal forces directly to the jaw bone.

This is where information about the dynamic behavior of the lower jaw brace would be important. Implants would have to be inserted (in terms of biomechanics) at those positions and in that direction in which the local loads during chewing or grinding and pressing are minimized. To this end, initially the motions of the lower jaw brace would have to be represented as a whole.

SUMMARY OF THE INVENTION

The present invention, in some embodiments, provides a measuring system which metrologically "decouples" the two jaw halves. This allows dynamic aspects, in particular the bending of the brace under the influence of a force can then be considered in a second step, to any first steps where information about local loads on the lower jaw is obtained.

Hence, the invention is based on the object to provide an improved apparatus of the generic type, which allows in particular the differentiated dynamic tracking and modeling of the behavior of the lower jaw, specifically during various chewing processes and motions like grinding or pressing.

According to the invention this object is achieved by an apparatus comprising the features of claim 1.

Useful embodiments of the inventive idea are defined in the respective dependent claims.

The invention includes the essential idea to go away from the previously suggested (dynamic) position determination of the lower jaw by means of a single receiver and transmitter holder of a position determining system which was assigned to the lower jaw as a whole, but assign separate position determining means to individual areas of the lower jaw instead. It further includes the idea to assign at least to the left side and the right side of the lower jaw a separate holder with corresponding left-sided and right-sided receiver and transmitter units and configure the associated evaluation unit to generate a differentiated dynamic image of the motions of the left side and the right side of the lower jaw. Basically, also a different distribution of the lower jaw into sections to be tracked individually in respect of their mobility is possible, for which purpose a correspondingly different assignment and, if necessary, greater number of holders for the corresponding receiver and transmitter elements have to be provided.

In one embodiment of the invention it is provided that the position determining system includes an ultrasonic measuring system which comprises ultrasonic transmitter units and ultrasonic receiver units, or an optical measuring system which comprises optical or IR markers or transmitter units and corresponding optical or IR receiver units.

In another embodiment of the invention the first evaluation unit has an input for mounting site information for specifying the respective mounting site of the second and third holder on the left and right sides of the lower jaw, and an evaluation component for processing this information with the signals from the receiver units. This configuration of the evaluation unit enables the dentist to mount the holders on the lower jaw in little time without having to exercise special care for an exactly predetermined position.

Basically, the second and third holder may be fixed to the left and right sides of the lower jaw in a paraocclusal manner, e.g. by using an adhesive. Advantageously, biting according to habit is still possible. Similarly, the first holder may be fixed to the upper jaw in a paraocclusal manner (e.g. by adhesion using a detachable adhesive).

In another embodiment the second and third holder are each configured for the detachable mounting on the lower jaw, in particular for the realization of a plurality of different mounting sites for the second and third holder. To this end, the holders may comprise, for instance, caps for placing them onto the respective row of teeth. This allows a particularly easy and fast mounting. Biting as usual is then no longer possible, however, as long as the patient wears the holders.

The above-mentioned embodiments of the evaluation unit and the holders configured as detachable holders can advantageously be combined such that the holders are suited to be fixed to different mounting sites and the respective mounting site is determined in the evaluation unit. The sequential selection of several mounting sites and the respective performance of a series of measurements allows an even better differentiation of the dynamic behavior of the lower jaw (differentiation of deformations section by section etc.).

In another embodiment a mounting aid for the precise placement of the second and third holder on the left side and right side of the lower jaw is provided, which forms part of the proposed system. This aid temporarily couples in particular the second and third holder rigidly to one another and can be detached after the mounting on the lower jaw is completed so as to release the second and third holder for independent motions. This facilitates the mounting of the holders, and the accuracy needed for the placement/orientation of the holders can be increased.

In another useful embodiment it is provided that the position determining system comprises coding means for differentiating between transmitted signals of left-sided transmitter units and those of right-sided transmitter units, or between signals of left-sided receiver units and right-sided receiver units. This allows the use of similar transmitter and receiver units, which are operated in particular on the same frequency and transmit similar receive signals. A differentiation is here made solely by the coding used in accordance with the embodiment.

In another embodiment the first holder comprises a set of left-sided transmitter or receiver units which are configured to communicate with the left-sided receiver and transmitter units on the second holder, and a set of right-sided transmitter or receiver units which are configured to communicate with the right-sided receiver and transmitter units on the third holder. As compared with a position determining system having a single set of transmitter or receiver units on the first holder this embodiment allows to increase the measuring accuracy and the immunity to interference of the position determination in certain cases.

The accuracy of information may be further increased by extending the measuring system, the position determining system comprising: an optical measuring system having an optical marker or active signal source provided on the first or second holder and an optical receiver unit provided on the respective other one of the first and second holder, in particular a camera, for receiving optical signals supplied by the marker or signal source, and a second evaluation unit for generating an additional measuring result of another motion component from the positional changes of the marker or optical signal source, which result from the motions of the lower jaw and are detected by the optical receiver unit, a synchronization unit which synchronizes the ultrasonic measuring system with the optical measuring system by synchronization signals, and a processing unit which combines the first and second measuring results which were supplied by the two measuring systems time-synchronously to form one resultant measuring result which represents the sequence of motions of the lower jaw relative to the upper jaw as a whole.

As compared to systems using exclusively ultrasonic measuring systems for the detection of motions and positions one advantage of this embodiment can be seen in that the measuring accuracy of the overall detection of motions in different directions of motion is no longer uncontrollably influenced by possible variations of the signal propagation times in the signal transmission lines and in the electronic ultrasonic measuring device.

In addition, the embodiment minimizes restrictions with respect to the accuracy of the measurement of a measured value in a specific direction of motion. Ultrasonic measuring systems are capable of supplying highly accurate measured values for motions in a determined, i.e. preferred depth coordinate. However, if the simultaneous detection of motions by the ultrasonic measuring system in another one than the preferred depth coordinate is desired the error of measurement is increased.

The combination of the two partial motion sequences respectively measured by an independent measuring system to one resultant overall measuring result ensures that the respective measuring system supplies only those measured values for a specific motion component as a contribution to the overall measuring result that have a high measuring accuracy. Combining the partial results supplied by the two measuring systems to one overall measuring result thus contributes to an improved measuring accuracy of the overall result.

The mode of operation and in particular the measured value acquisition of both measuring systems are to be adjusted to one another in such a way that the generated measuring results for the first and second motion component can be converted into a common coordinate system so as to represent therewith a resultant end result that covers the entire sequence of motions composed of the first and second motion component.

According to one embodiment of the optical receiver unit of the optical measuring system an electronic camera system having at least one camera is used. The camera is preferably attached at the face-bow in a fixed relationship relative to the upper jaw. This may be done on the first holder which is fixed to the head of the patient. The camera may be an infrared camera. Thus, infrared signals can be received which are transmitted, for instance, by infrared light emitting diodes. However, basically also an optical receiver unit may be used which is not placed on the head of the test object, but spaced apart from same. In this case, additional means for correcting (minimal) motions of the head during the measurements are to be provided. In a specific embodiment the correcting means include image processing means for identifying motions of characteristic elements of the head, e.g. the ears. The correcting means may also include marker elements which sit on a holder that is stationarily fixed relative to the head and is fixed to the upper jaw or may sit on the root of the nose.

In a further development of the apparatus proposed at least one optical active or passive marker element may be provided on one of the holders.

A passive marker element, i.e. a marker element that does not emit own optical signals is, for instance, a surface on whose surface area a geometric pattern is reproduced which can be recorded by the optical measuring system. If passive optical marker elements are used it may be sensible to expose them to radiation by an integrated illumination unit. This may be, for instance, an infrared illumination if infrared-sensitive cameras are used as optical receiver units. The active marker element, i.e. a marker element that transmits signals, may be (infrared) light emitting diodes which can be recorded by an infrared camera. Moreover, the arrangement of the patterns or light spots on the surface of the optical marker element at a certain distance allows an easy calibration of the camera system.

To allow the measured values supplied by the two measuring systems to be converted into a common coordinate system it is necessary to time-synchronize the mode of operation, in particular the acquisition of measured values during the detection of motion, of the ultrasonic measuring system with the optical measuring system. Another aspect for the necessity for the time-synchronous transmission of the acquired measured values to an evaluation unit of a processing unit can be seen in that non-defined delay times may arise due to different processing times on account of the hardware and software used in the different measuring systems. The consequence of this would be that the measuring results generated by the respective measuring systems, when processed to a resultant measuring result that represents the entire sequence of motions for a first and a second motion component, would no longer be uniquely assignable.

In a preferred embodiment of the synchronization unit it is, therefore, provided that same acts as a synchronization signal generator which generates and transmits via a wired or wireless synchronization signal transmission path between the ultrasonic measuring system or optical measuring system and the evaluation unit of the respective measuring system the necessary synchronization signals, so that both measuring systems work synchronously.

Another possibility of synchronizing the mode of operation of both measuring systems would be the transmission of a synchronization signal (e.g. an infrared light pulse) from the ultrasonic measuring system to the optical measuring system, or vice versa, at least at one point in time during the measurement, providing this synchronization signal with coding features, and superimposing (modulating) this coding on the measuring signals of both measuring systems. At the same time, it must be ensured that the receiver and evaluation unit of the respective measuring system receiving the synchronization signal comprises corresponding means that decouple the received synchronization signal from the received measuring signal, in particular by decoding.

Also, it would be conceivable, however, that a similar synchronization signal is transmitted by the respective measuring system or the synchronization unit not during the acquisition of the measured value, but as a starting signal, e.g. as an infrared signal. Where appropriate, a coding of the signal can then be waived. If the synchronization is carried out only for a short time during the acquisition of the measured value both measuring systems need to have a stable time basis internally (e.g. a quartz time basis) for allowing the timings to be reconstructed synchronously with one another.

A particularly simple possibility of time-synchronizing both measuring systems is the use of an additional illumination unit which is preferably installed on one of the ultrasonic receiver units. The illumination unit may be a light emitting diode or a flash lamp. The light emitting diode emits, for instance, a pulsed light, i.e. the light emitting diode is adapted to always emit a light pulse exactly at the time when one or only the first of the sequentially working ultrasonic transmitter units transmits a corresponding pulse. Thus, it is possible to synchronize the two measuring systems with one another in such a way that the measuring results of the respective motion components are transmitted simultaneously to the processing unit for the further processing thereof.

BRIEF DESCRIPTION OF THE DRAWINGS

Advantages and useful features of the invention are also given in the following sketch-like description of exemplary embodiments, which are schematically illustrated in the appended figures. In the figures.

DETAILED DESCRIPTION OF THE DRAWINGS

Figure 1:
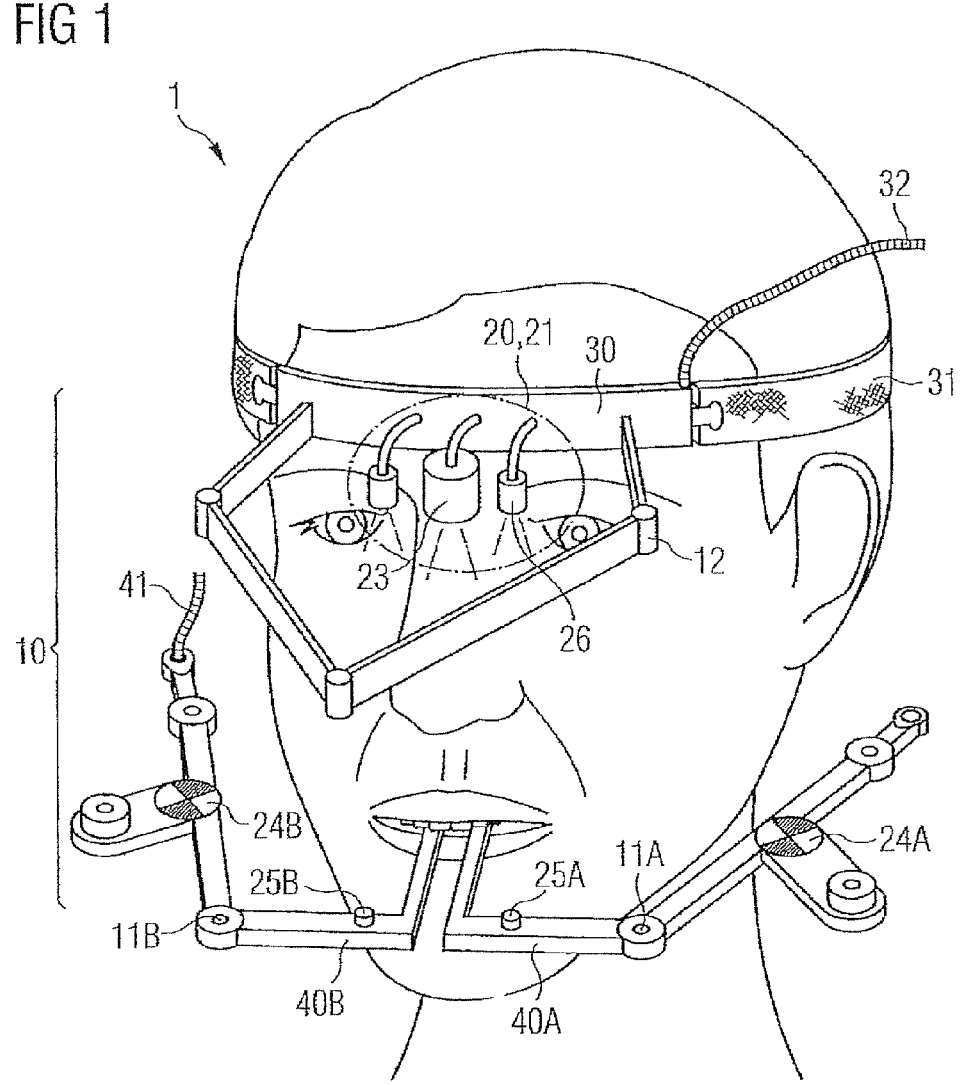
FIG. 1 shows a sketch-like partial view of an arrangement for the detection of motions of the lower jaw relative to the upper jaw of a human being.

FIG. 1 shows parts of an apparatus 1 fixed to the head of a patient. An ultrasonic measuring system 10 and an optical measuring system 20 of the apparatus are combined with one another. Essential components of the two measuring systems are held by a first holder 30 and a second and third holder 40A, 40B.

In the embodiment shown ultrasonic receiver units 12 are attached to the first holder 30, which is held substantially (i.e. sufficiently for the relevant measurements) stationarily on the forehead of the patient by an elastic head band 31. Further, an optical receiver unit 21 is mounted on the first holder 30, which comprises a high-resolution camera 23 and two LED lamps 26 as illumination units. In the embodiment shown a connecting cable 32 serves the power supply of the camera 23 and the lamps 26 and, furthermore, the transmission of image signals obtained by the camera and other measured signals (see below) to remotely arranged evaluation units. Instead of using an external wired power supply rechargeable batteries may be installed in the first holder 30, and the wired signal transmission may be replaced by a wireless signal transmission (e.g. by a Bluetooth path) so that the cable 32 may be omitted, allowing the patient to move more freely.

Attached to the second and third holder 40A, 40B, which are fixed to the patient's lower jaw in a temporarily rigid manner, are ultrasonic transmitter units 11A and 11B which generate the corresponding ultrasonic signals. A cable 41 serves the power supply and, where appropriate, the synchronization of the ultrasonic transmitters 11A, 11B. This cable, too, may be waived in an alternative embodiment if a battery or rechargeable battery power supply is provided in the second holder 40. The generated ultrasonic signals are received by the ultrasonic receiver units 12 on the first holder 30 and transmitted to a (non-illustrated) evaluation unit of the ultrasonic measuring system 10. The evaluation unit of the ultrasonic measuring system calculates from the received measured values—independently from the left- and right-sided signal transmission for the left and the right side of the lower jaw—a first measuring result, especially for a first motion component.

In addition, a surface with a pattern as an optical passive marker element 24A, 24B is placed on the second and third holder 40A, 40B. The arrangement of the pattern on the surface, with defined distance areas, allows a calibration of the individual cameras 23. The pattern reproduced on the surface is recorded by the cameras 23 of the optical receiver unit 21 and supplies corresponding signals to a non-illustrated evaluation unit of the optical measuring system 20 if the second holder 40A and/or the third holder 40B move relative to the first holder 30. The evaluation unit of the optical measuring system 20 generates therefrom—again, separately for the left-sided and right-sided lower jaw—a measuring result, specifically for a second motion component, which is then transmitted to a non-illustrated processing unit (see FIG. 2).

FIG. 1 further shows that light emitting diodes 25A and 25B are each placed on the second holder 40A and the third holder 40B. The light emitting diodes 25A, 25B can be driven, for instance, to emit a light pulse only if one of the ultrasonic transmitter units 11A, 11B emits a pulse. In this simple manner it is possible to time-synchronize the ultrasonic measuring system 10 with the optical measuring system 20.

Figure 2:
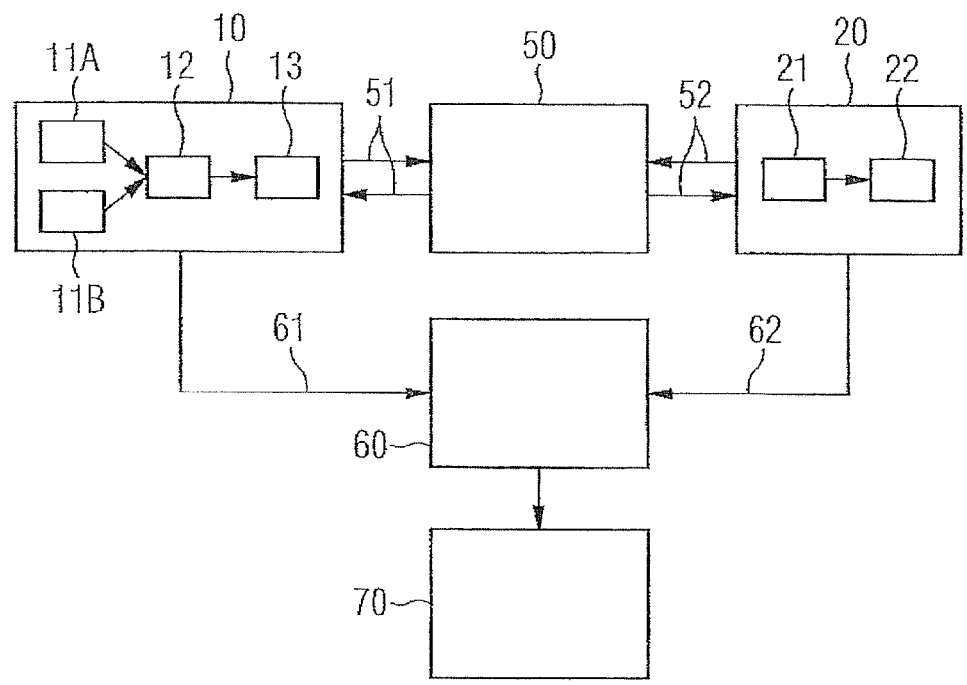
FIG. 2 shows a system-oriented block diagram of this arrangement.

FIG. 2 schematically shows an apparatus 1 comprising the ultrasonic measuring system 10, the optical measuring system 20, a synchronization unit 50, a processing unit 60 and a display unit 70.

The ultrasonic measuring system 10 includes the ultrasonic transmitter units 11A, 11B, the ultrasonic receiver units 12 and an evaluation unit 13. The ultrasonic receiver units 12 receive the signals successively transmitted by the ultrasonic transmitter units 11A, 11B, each with a specific coding which allows the differentiation between the signals transmitted by the left-sided transmitter units 11A on the one hand and by the right-sided transmitter units 11B on the other hand. In the evaluation unit 13 of the ultrasonic measuring system 10 the received signals are each processed to a left-sided and a right-sided first signal which represents a first measuring result for a first motion component. This first measuring result—which, in reality, has a structure that reflects the sequences of motions of the left and right sections of the lower jaw in a differentiated manner—is supplied to the processing unit 60 via an interface 61.

The optical measuring system 20 comprises the optical receiver unit 21 with the camera 23 and an evaluation unit 22. The images taken by the camera 23 are processed in the evaluation unit 22 to a second signal which represents a second measuring result for a second motion component. This second measuring result, too, which likewise reflects the differentiated mobility of the left and right halves of the lower jaw—is supplied to the processing unit 60 via a second interface 62.

The synchronization unit 50, which, in the embodiment of FIG. 2, is arranged between the two measuring systems, has the task to time-synchronize the ultrasonic measuring system 10 with the optical measuring system 20. The synchronization unit 50 comprises a synchronization signal generator and an IR transmit element coupled to same which serves as a synchronization signal transmitter for synchronization signals via synchronization signal transmission paths 51, 52 as interfaces to the first and second measuring system 10, 20. The synchronization signal ensures that the acquisition of the measured value and the processing thereof of both measuring systems is time-synchronized so that the measuring results for the first and second motion component, which are generated by the respective evaluation units 13 and 22 of the two measuring systems 10 and 20, are transmitted time-synchronously to the processing unit 60 so to allow the representation of the measuring results in a common coordinate system.

The processing unit 60 processes the measuring results for the respective motion components, which were supplied by the two measuring systems, to one resultant overall measuring result which is represented in a common coordinate system on the display unit 70.

Figure 3:
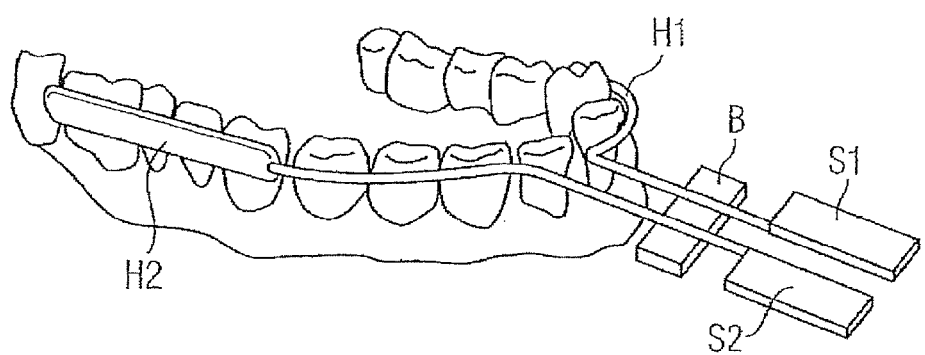
FIG. 3 shows a sketch-like illustration of a mounting alternative of the second and a third holder of an arrangement according to the invention.

FIG. 3 shows in a sketch the lower jaw of a human being with two holders H1, H2 fixed by means of a dental adhesive (not shown), each of which carries a position sensor system S1 and S2. In the state as illustrated the two holders H1, H2 are additionally connected by a connecting clamp B, which is a mounting aid to allow an easier and precise placement of the holders. After the fixing, clamp B is removed and the holders H1, H2 follow the left-sided and right-sided motion of the lower jaw without obstruction.

The mounting surface (not separately designated) at the end of the holders in FIG. 3 may be replaced, in a modified embodiment, by a cap which is pulled over the corresponding teeth and retains the holder safely on the lower jaw, e.g. by means of a predetermined elasticity. If a cap of this type (or a similar detachable holding means) is adapted to fit on the lower jaw at different positions the point of the mechanical connection between the lower jaw and the respective holder can thus be predetermined as required, and can also be varied selectively for performing a series of measurements at different fixing locations.

The realization of the invention is not limited to the described examples and emphasized aspects, but is possible also with a plurality of modifications that are within the framework of the competent action of the skilled person.

The invention claimed is:

1. Apparatus for detecting motions of a lower jaw relative to the upper jaw of a vertebrate, comprising:
   a position determining system comprising a first element in operative communication with a second element;
   a first holder (30) for placement relative to the upper jaw on the head of the vertebrate, and in mechanical communication with the first element of the position determining system (1),
   a second holder (40A) for placement relative to the left side of the lower jaw in mechanical communication with the second element of the position determining system,
   a third holder (40B) for placement relative to the right side of the lower jaw in mechanical communication with the second element of the position determining system,
   at least a portion of each of the second holder and the third holder (40A, 40B) are configured for detachably mounting at least proximate to the lower jaw;
   a connector configured for temporarily coupling the second holder with the third holder during placement of the second holder and the third holder relative to the lower jaw, the connector being separable from the second holder and the third holder, such that upon separation of the connector from the second holder and the third holder, the second holder and the third holder move independently with respect to each other, and,
   a first evaluation unit (13) for processing signals from the position determining system, for generating a differentiated dynamic image of the motions of the left and right sides of the lower jaw from relative positional changes of the second element of the position determining system of the second holder and the third holder, with respect to the position of the first element of the position determining system of the first holder, which are associated with the motions of the lower jaw and are detected by the position determining system.

2. Apparatus according to claim 1, wherein the position determining system includes an ultrasonic measuring system (10) comprising: at least one ultrasonic transmitter unit and at least one ultrasonic receiver unit for generating at least one measurement from the positions of the at least one ultrasonic transmitter unit with respect to the at least one ultrasonic receiver unit.

3. Apparatus according to claim 2, wherein the first evaluation unit (13) includes: 1) an input for receiving mounting site information indicating the location of the respective mounting site of each of the second holder and the third holder (40A, 40B) on the left and right sides of the lower jaw, and, 2) an evaluation component for processing the mounting site information with the signals received by the at least one ultrasonic receiver unit.

4. Apparatus according to 2, wherein the at least one ultrasonic transmitter unit includes a left side ultrasonic transmitter unit and a right side ultrasonic transmitter unit, and the at least one ultrasonic receiver unit includes a left side ultrasonic receiver unit and a right side ultrasonic receiver unit, and, the position determining system additionally comprises: a coding analyzer for differentiating: 1) between transmitted signals of the left-side ultrasonic transmitter unit and the right-side ultrasonic transmitter unit, in accordance with the respective codes of the transmitted signals, and, 2) between received signals of the left-side ultrasonic receiver unit and the right-side ultrasonic receiver unit, in accordance with the respective codes of the received signals.

5. Apparatus according to 4, wherein the first element of the position determining system is associated with the first holder (30) and includes the left-side ultrasonic receiver unit (12) and the right side ultrasonic receiver unit (12); and, the second element of the position determining system includes the left side ultrasonic transmitter unit (11A) associated with the second holder (40A), and the right side ultrasonic transmitter unit (11B) associated with the third holder (40B), the left side ultrasonic receiver unit and the right side ultrasonic receiver unit being configured to operatively communicate with the respective left-side ultrasonic transmitter unit, and the right-side ultrasonic transmitter unit.

6. Apparatus according to claim 1, wherein the first holder is configured to be placed away from the head of the vertebrate and additionally comprises correcting means to identify and arithmetically account for motions of the head in the evaluation of the signals from the receiver units which are generated from a motion of the lower jaw.

7. Apparatus according to claim 6, wherein the correcting means include an image processor to identify motions of elements of the head, based on a comparison of camera images.

8. Apparatus according to claim 6, wherein the correcting means comprises marker elements which are to be fixedly arranged on the head of the vertebrate by means of a suitable holder.

9. Apparatus according to claim 4, wherein the first evaluation unit (13) is configured for evaluating the signals from the ultrasonic receiver units, each of the ultrasonic receiver units being assigned to a specified placement on the second holder (40A) and the third holder.

10. Apparatus according to claim 4, wherein the first element of the position determining system is associated with the first holder (30) and includes the left-side ultrasonic transmitter unit (12) and the right side ultrasonic transmitter unit (12); and, the second element of the position determining system includes the left side ultrasonic receiver unit (11A) associated with the second holder (40A), and the right side ultrasonic receiver unit (11B) associated with the third holder (40B), the left side ultrasonic transmitter unit and the right side ultrasonic transmitter unit being configured to operatively communicate with the respective left-side ultrasonic receiver unit, and the right-side ultrasonic receiver unit.

11. Apparatus according to claim 2, wherein the position determining system additionally comprises: an optical measuring system (20) comprising: an optical signal source and corresponding optical signal receiver units.

12. Apparatus according to claim 11, wherein the optical signal receiver unit (21) is in communication with the first holder, and the optical signal source (24, 25) is in communication with the second holder, and, the optical measuring system additionally comprises:
- a second evaluation unit (22) for generating at least one measurement from positional changes of the optical signal source with respect to the optical signal receiver unit, which result from the motions of the lower jaw and are detected by the optical signal receiver unit (21);
- a synchronization unit (50) to synchronize the ultrasonic measuring system (10) with the optical measuring system (20) by synchronization signals; and,
- a processing unit (60) to combine each of the at least one measurement from the ultrasonic measuring system and the optical measuring system to form one measuring result which represents the sequence of motions of the lower jaw relative to the upper jaw.

13. Apparatus according to claim 12, wherein the optical signal source includes at least one optical active or passive marker element (24, 25) to calibrate the optical receiver unit (21), the at least one optical active or passive marker element including a surface with a pattern which is detectable by the optical receiver unit (21).

14. Apparatus according to claim 12, additionally comprising: an illumination unit (26) to illuminate the marker element (24) and the ultrasonic transmitter unit (11) for synchronizing the ultrasonic measuring system (10) with the optical measuring system (20).

15. Apparatus according to claim 12, wherein the ultrasonic measuring system (10) and the optical measuring system (20) additionally comprise a synchronization signal transmitter for transmitting a synchronization signal therebetween, the synchronization signal being modulated on the measured signal used by the ultrasonic measuring system and the optical measuring system respectively.

16. Apparatus according to claim 12, wherein the optical signal source is selected from the group consisting of: an optical marker, and Infra Red (IR) marker, and an optical signal transmitter, and the optical signal receiver units selected from the group consisting of optical receiver units, IR receiver units, and a camera.

17. Apparatus according to claim 1, wherein the first holder (30) is configured to be detachably fixed to the upper jaw of the vertebrate.

* * * * *